US008343137B2

(12) United States Patent
Calimeri et al.

(10) Patent No.: US 8,343,137 B2
(45) Date of Patent: Jan. 1, 2013

(54) MEDICAL CONNECTOR

(75) Inventors: Aldo Calimeri, Capo d'Orlando (IT); Stefano Ganzerli, Medolla (IT); Eugenio Lombardo, Ponte Nelle Alpi (IT); Matteo Manfredini, Modena (IT)

(73) Assignee: Gambro Lundia AB, Lund (SE)

( * ) Notice: Subject to any disclaimer, the term of this patent is extended or adjusted under 35 U.S.C. 154(b) by 251 days.

(21) Appl. No.: 12/934,448

(22) PCT Filed: Apr. 1, 2008

(86) PCT No.: PCT/IB2008/000759
§ 371 (c)(1),
(2), (4) Date: Nov. 3, 2010

(87) PCT Pub. No.: WO2010/061234
PCT Pub. Date: Jun. 3, 2010

(65) Prior Publication Data
US 2011/0137294 A1    Jun. 9, 2011

(51) Int. Cl.
*A61M 25/16* (2006.01)
*A61M 25/18* (2006.01)

(52) U.S. Cl. ......... 604/534; 604/533; 604/535; 604/538

(58) Field of Classification Search .................. 604/533, 604/534, 535, 536, 538, 539; 285/305, 403, 285/921
See application file for complete search history.

(56) References Cited

U.S. PATENT DOCUMENTS

| 7,666,170 B2 * | 2/2010 | Guala ........................... 604/249 |
| 2005/0146136 A1 | 7/2005 | Kawamura et al. |

FOREIGN PATENT DOCUMENTS

| EP | 0 775 501 A1 | 5/1997 |
| EP | 0 953 365 A1 | 11/1999 |
| EP | 1 552 858 A1 | 7/2005 |
| JP | 2005-231453 A | 9/2005 |
| JP | 2005-329040 A | 12/2005 |

* cited by examiner

*Primary Examiner* — Bhisma Mehta
(74) *Attorney, Agent, or Firm* — Pearne & Gordon LLP

(57) ABSTRACT

A medical connector, of a female luer type, comprises an external tubular body (4) which contains an internal tubular body (2) free to rotate about an axis thereof. The external tubular body exhibits a screw-coupling surface. The internal tubular body exhibits a conical luer seal surface. An insert (5), which has a pawl (9) snap-fitted in a window (8) afforded on the external tubular body, constrains the two tubular bodies solidly to one another, in an axial displacement direction. The connector is used to connect a blood line to a blood port of a dialyser, preventing the blood line from twisting on itself and kinking.

31 Claims, 13 Drawing Sheets

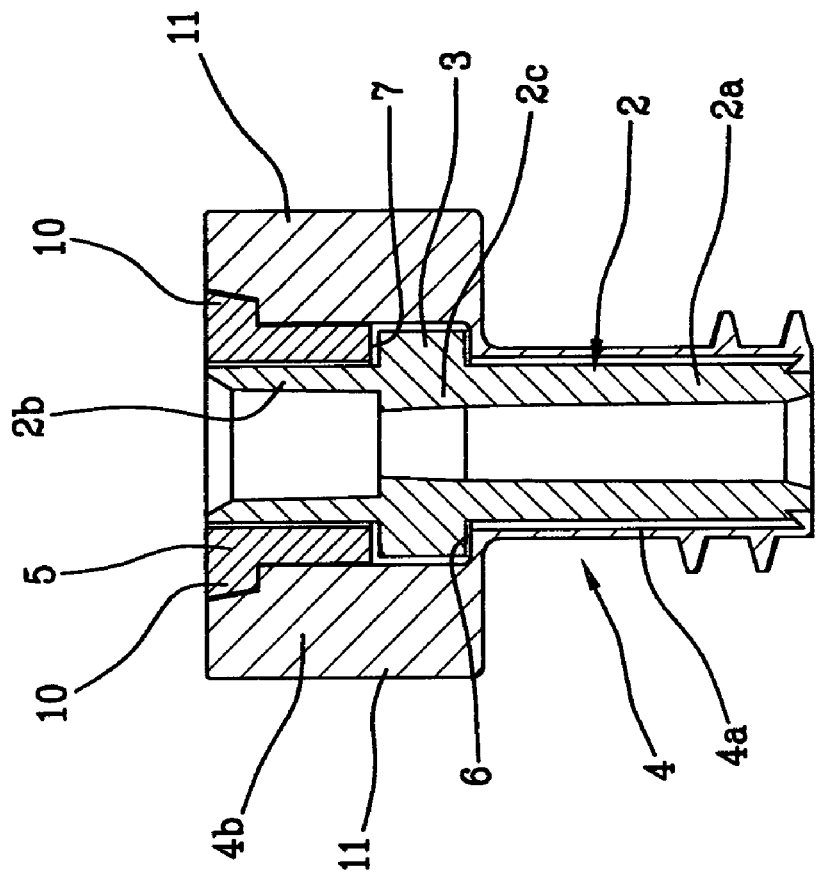
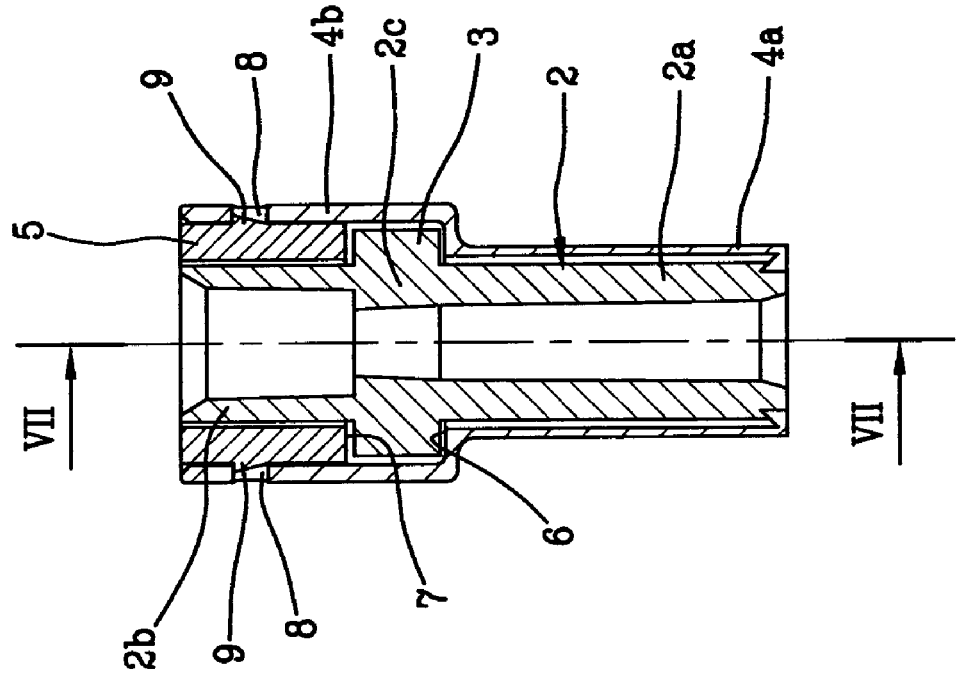
FIG 7
FIG 6

FIG 8
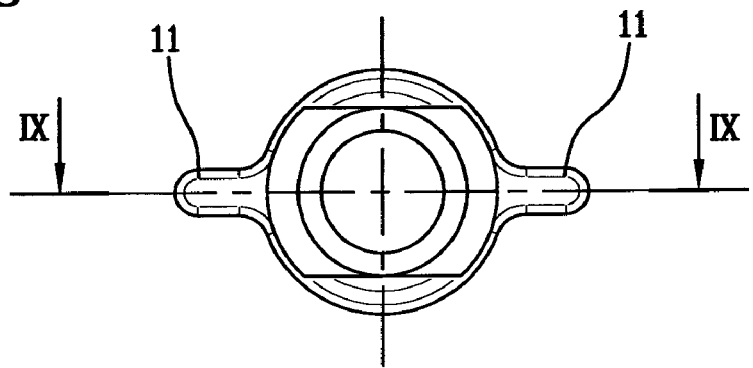
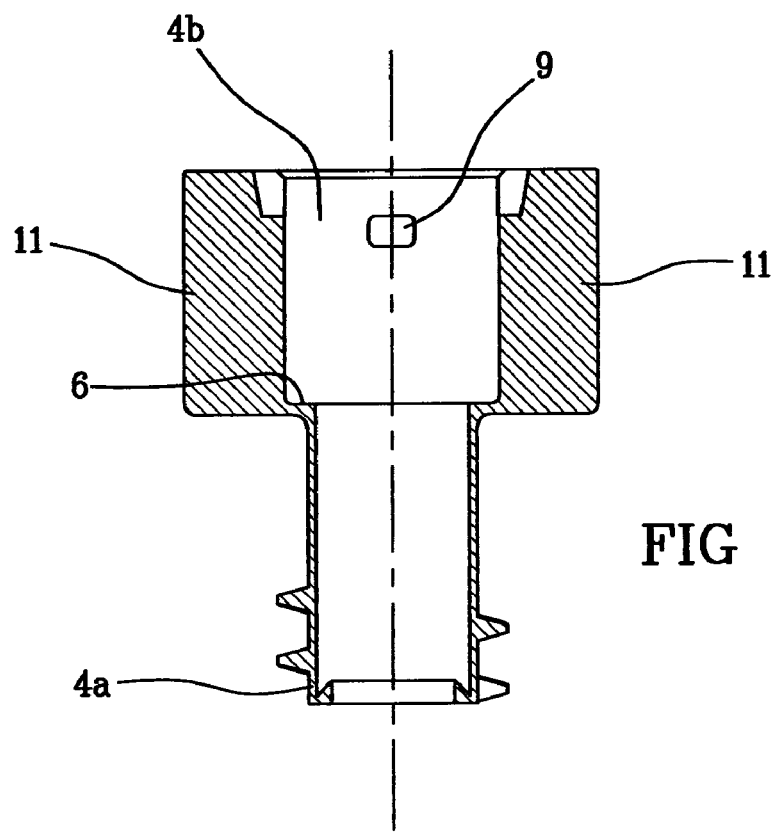
FIG 9
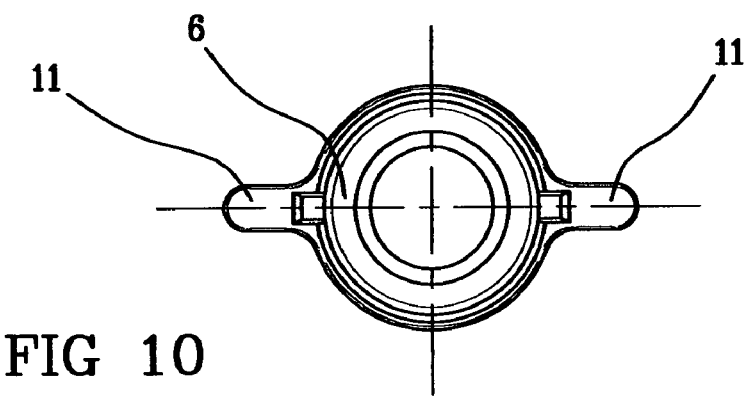
FIG 10

FIG 14
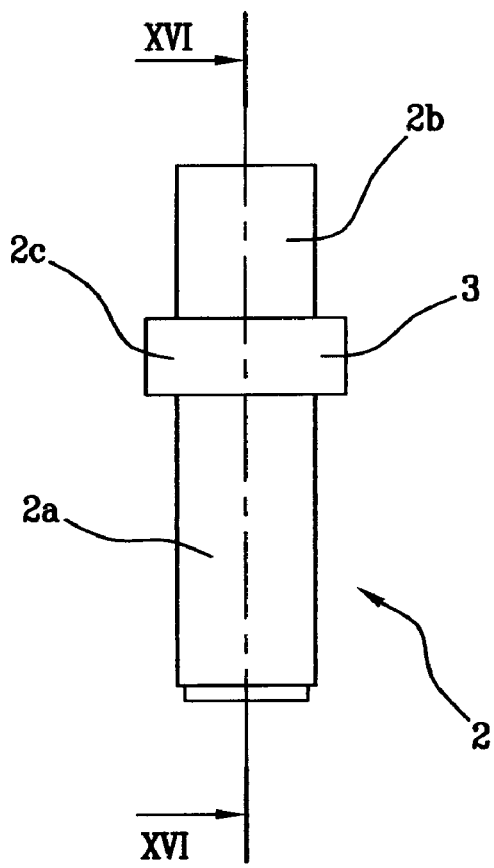
FIG 16
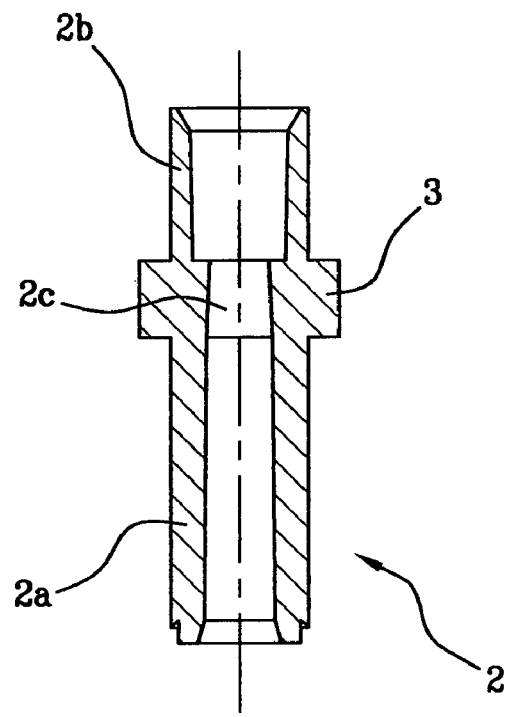
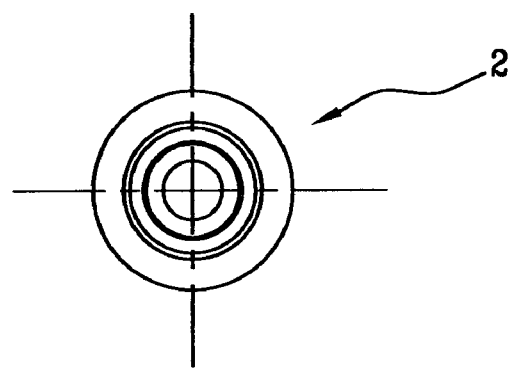
FIG 15

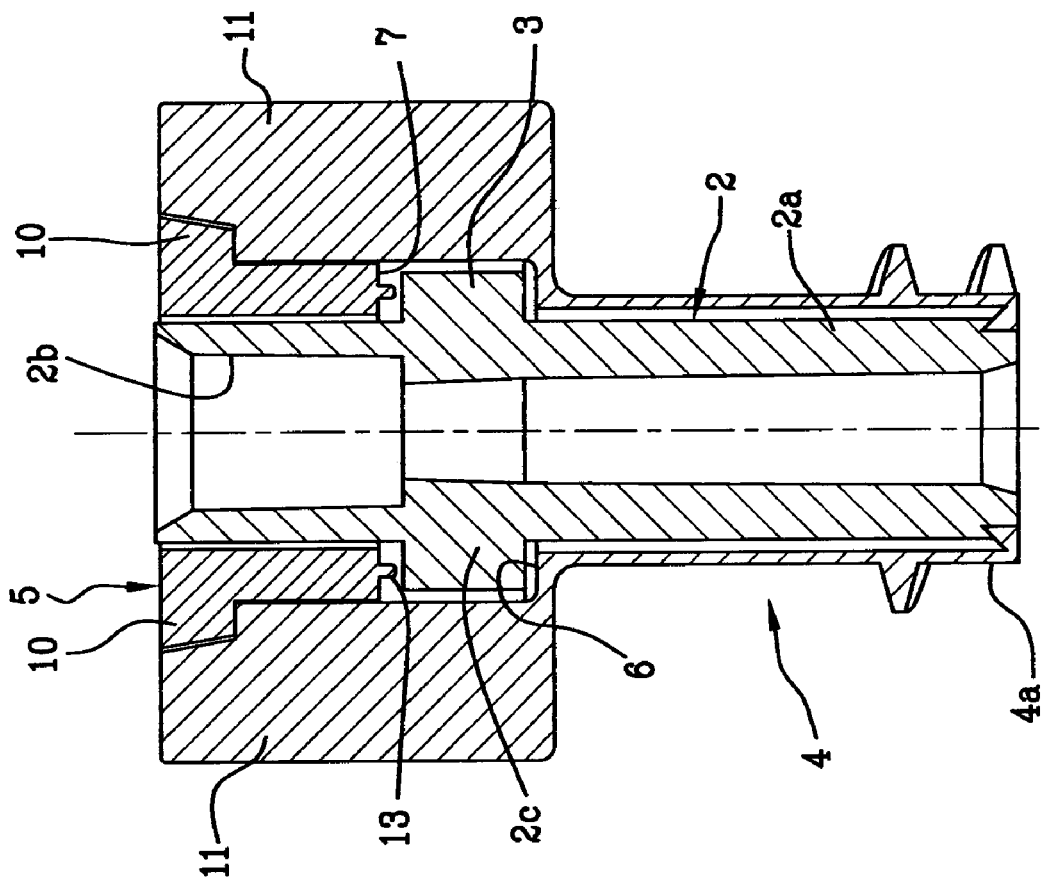
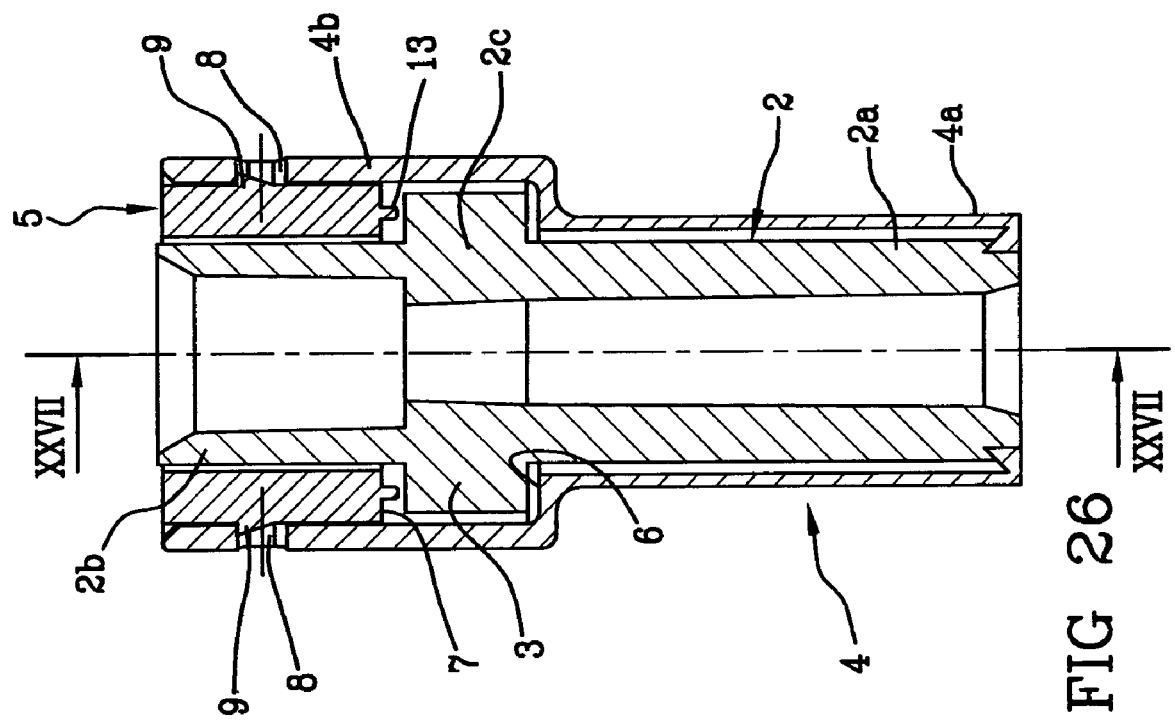

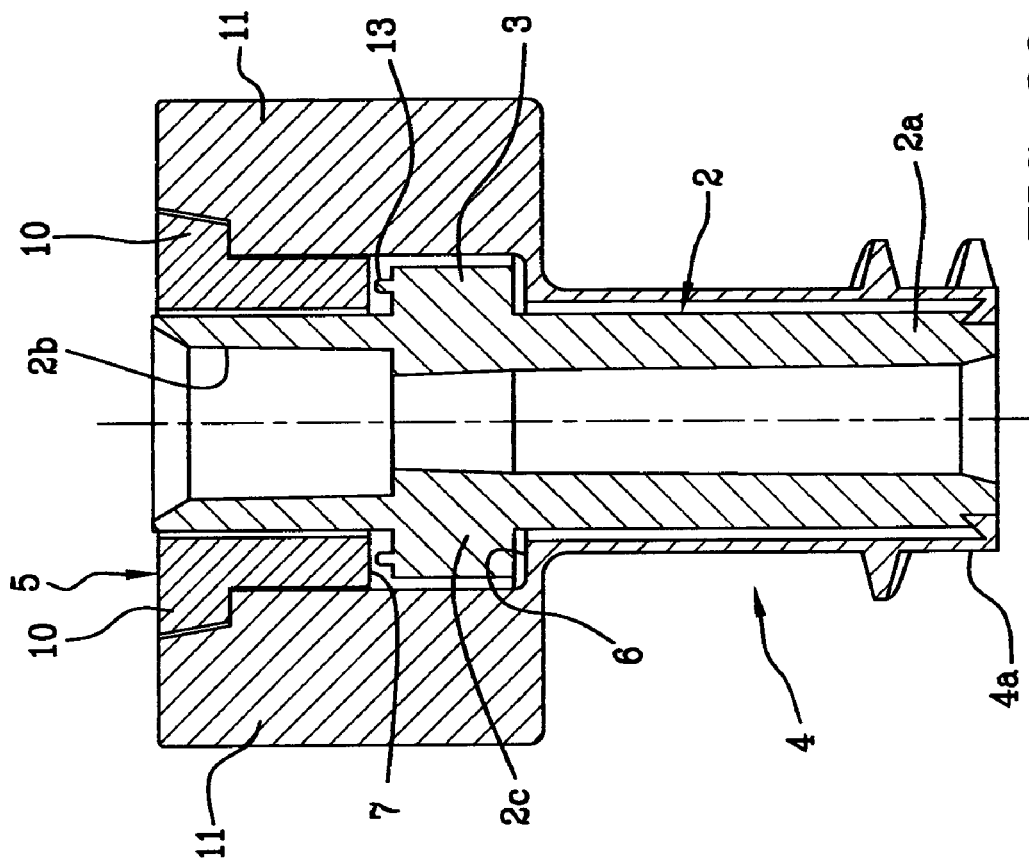
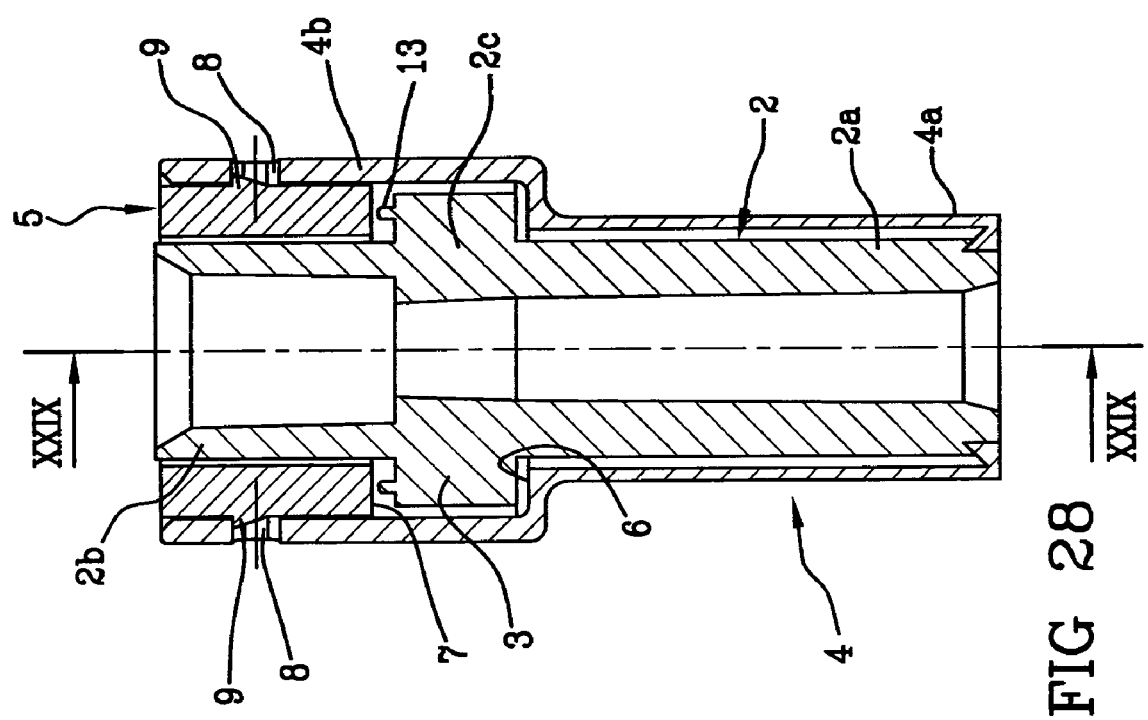

MEDICAL CONNECTOR

BACKGROUND OF THE INVENTION

The invention relates to a medical connector.

In particular, the invention relates to a medical connector which connects two fluid containing elements (in which each fluid containing element can comprise, for example an extracorporeal blood transport tube, an extracorporeal blood treatment device, a medical fluid transport tube, a batch container of medical fluid, etc.), such as to avoid that on coupling at least one or even better neither of the two fluid container elements does not have to rotate upon itself, such as to reduce the risks due to this rotation, such as for example the risk of torsional kinking, or another type of occlusion, in a case in which the fluid container element is a flexible tube. In particular, the medical connector can be a female luer connector.

Specifically, but not exclusively, the invention can be usefully applied to connect an extracorporeal blood circuit (for example a set of fluid transport lines for kidney dialysis, hereinafter referred-to as a "dialysis set") to an extracorporeal blood treatment (for example a dialyser).

The prior art comprises JP 2004-41612, which describes a female luer connector for connecting a blood transport tube with a male luer port of a dialyser, in which, when the connecter is connected to the dialyser port, a sleeve integrally coupled with the tube is compressed between the connector and the port and thus fixed to the port itself. This solution avoids the tube's being twisted on connection, such as to reduce the risk of kinking (in particular torsional kinking) of the tube.

The prior art further comprises various medical connector each provided with at least two parts of which one is rotatable with respect to the other.

EP 953365 describes a female luer connector having an internal sleeve which bears a truncoconical internal sealing surface with a luer conicity, and an external sleeve which bears an external surface with a screw coupling. The two sleeves are freely rotatable with respect to one another such that a tube, having an end connected to an end of the internal sleeve, is not twisted while the external sleeve is screwed to a male luer. Relative axial displacement between the two sleeves is prevented by a joint formed by an annular radial projection borne by a sleeve inserted in an annular channel afforded in the other sleeve.

EP 775501 describes a female luer having an internal sleeve, made of a relatively soft material, which is twistable with respect to an external sleeve made of a stiffer material. The two sleeves are axially conjoined by means of an annular projection borne by the external sleeve and snap-fitted in an annular channel afforded on the internal sleeve.

EP 1552858 describes a female luer connector having two freely and reciprocally-twistable sleeves and reciprocally constrained in an end of the internal sleeve, and a stopper fixed to the opposite end of the internal sleeve. The external sleeve has a limited freedom of axial movement which is defined by the difference between the axial distance between the flange and the stopper minus the axial length of the external sleeve. When the female luer connector is connected to a male luer connector, the internal sleeve is subjected to extension stress.

JP 2005-329040 describes a female luer connector with an internal sleeve and an external sleeve which are freely twistable with respect to one another in an axial direction due to a projection, borne on one of the two sleeves, which is engaged in a recess afforded in the other. A degree of axial play exists due to the fact that the axial length of the projection is less than the axial length of the recess. The connector of JP 2005-329040 should lead to a lower risk of unexpected disconnection with respect to the connector of EP 1552858.

SUMMARY OF THE INVENTION

An aim of the present invention is to provide a medical connector which can connect two fluid container elements to one another with a reduced risk of drawbacks due to the twisting of at least one of the two elements.

An advantage of the invention is to provide a medical connector which is constructionally simple, reliable and economical.

A further advantage is to make available a medical connector which is able to ensure a stable, enduring and reliable connection between two fluid container elements.

A further advantage still is to give rise to a medical connector realised in several parts which can be assembled rapidly and in a simple way.

These aims and advantages are all attained by the invention as it is characterised in one or more of the accompanying claims.

Further characteristics and advantages of the present invention will better emerge from the detailed description that follows, of at least an embodiment of the invention, illustrated by way of non-limiting example in the appended figures of the drawings.

BRIEF DESCRIPTION OF THE DRAWINGS

The description will be made with reference to the accompanying figures of the drawings, provided by way of indication and therefore non-limiting.

FIG. 6 is a longitudinal section of a second embodiment of the medical connector of the invention.

FIG. 7 is a section along line VII-VII of FIG. 6.

FIGS. from 8 to 13 are views and sections of a component (external tubular body 4) of the connector of FIG. 6.

FIGS. from 14 to 16 some views and sections of a further component (internal tubular body 2) of the connector of FIG. 6.

FIGS. from 17 to 19 illustrate some views and sections of a further component (insert 5) of the connector of FIG. 6.

Figure 20:
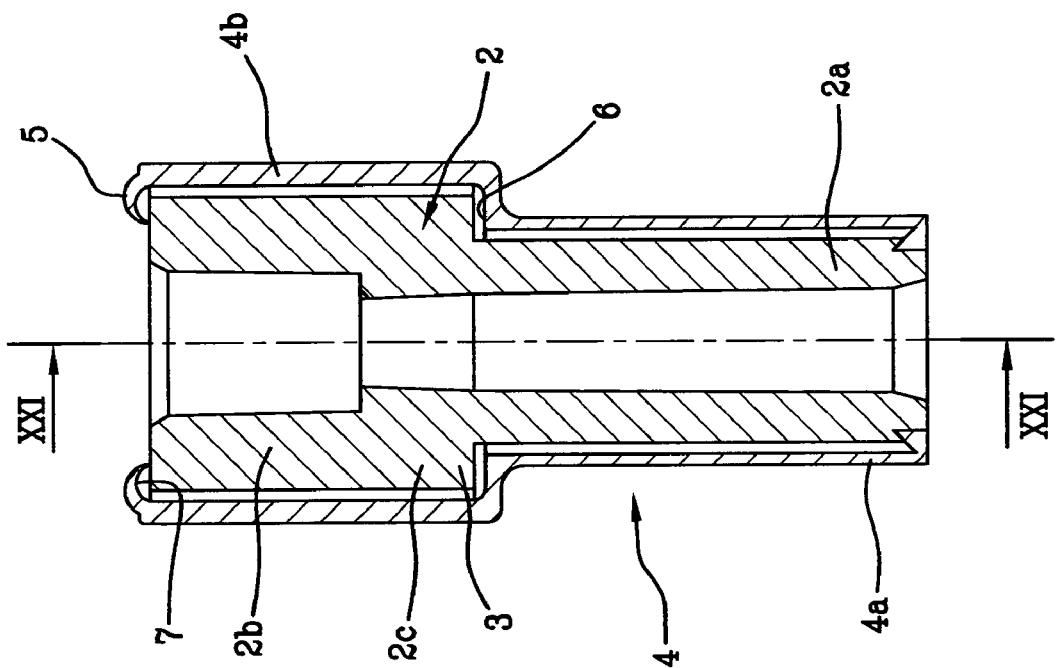

FIG. 20 is a longitudinal section of a third embodiment of the medical connector of the invention.

Figure 21:
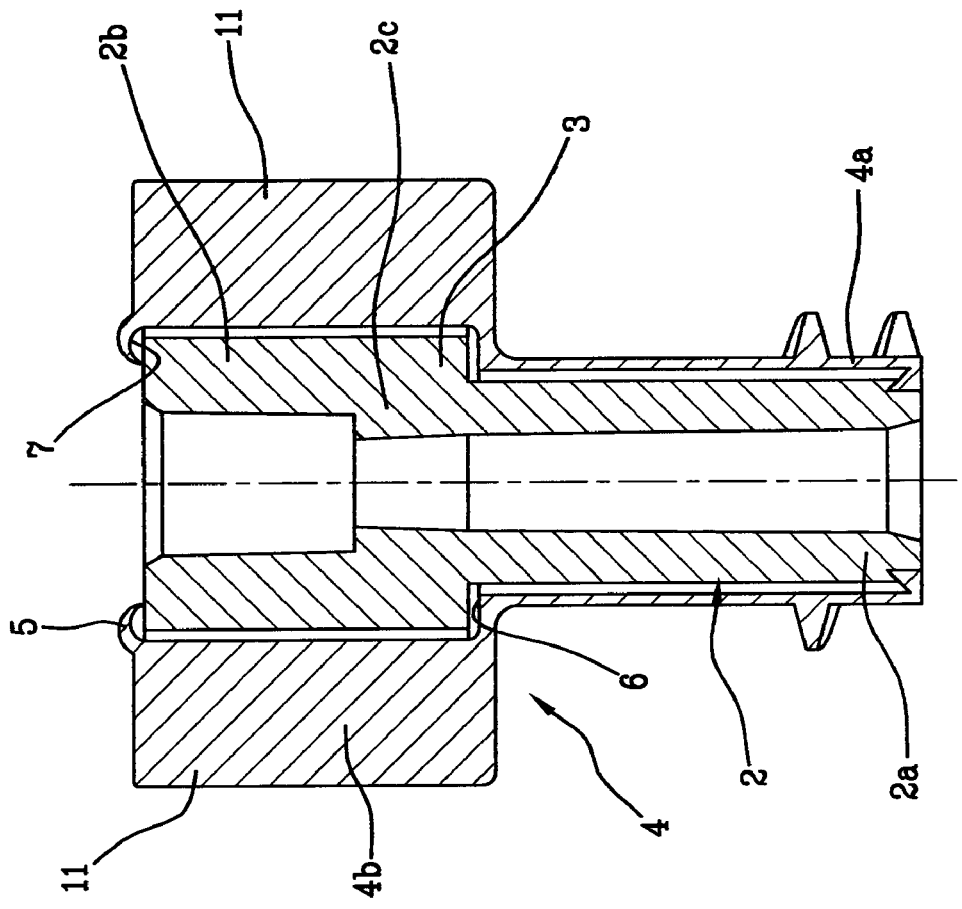

FIG. 21 is a section along plane XXI-XXI of FIG. 20.

Figure 23:
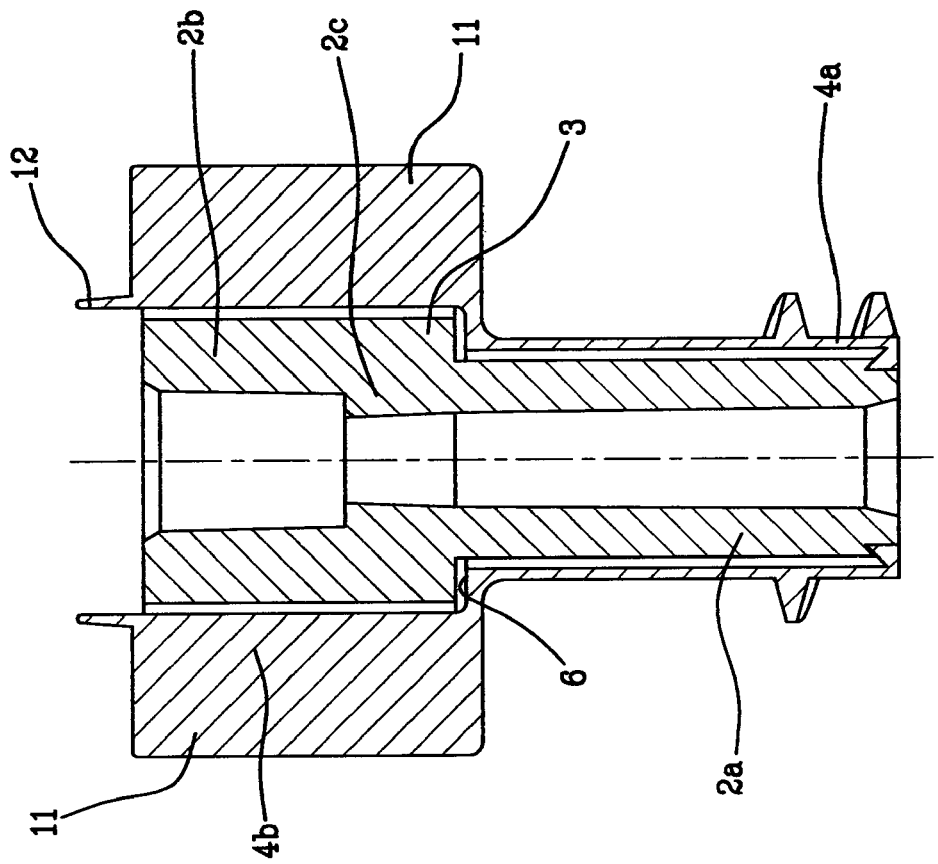
Figure 22:
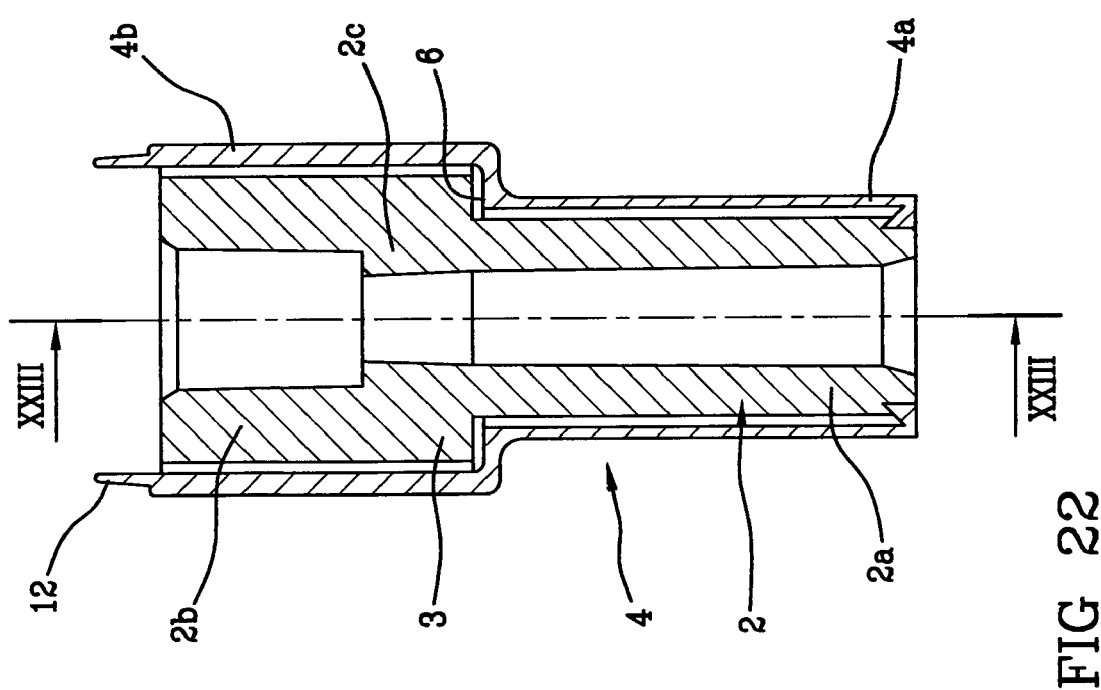

FIGS. 22 and 23 show the connector of FIGS. 20 and 21 in a realisation stage which precedes the plastic deformation of the projecting element for realising the insert 5.

Figure 24:
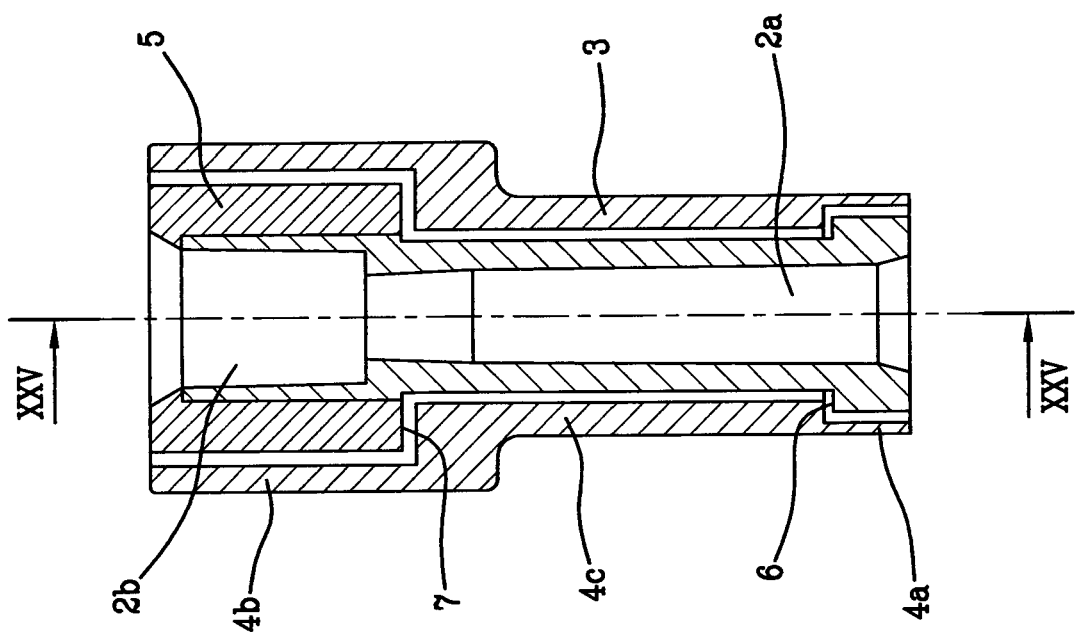

FIG. 24 is a longitudinal section of a fourth embodiment of the medical connector of the invention.

Figure 25:
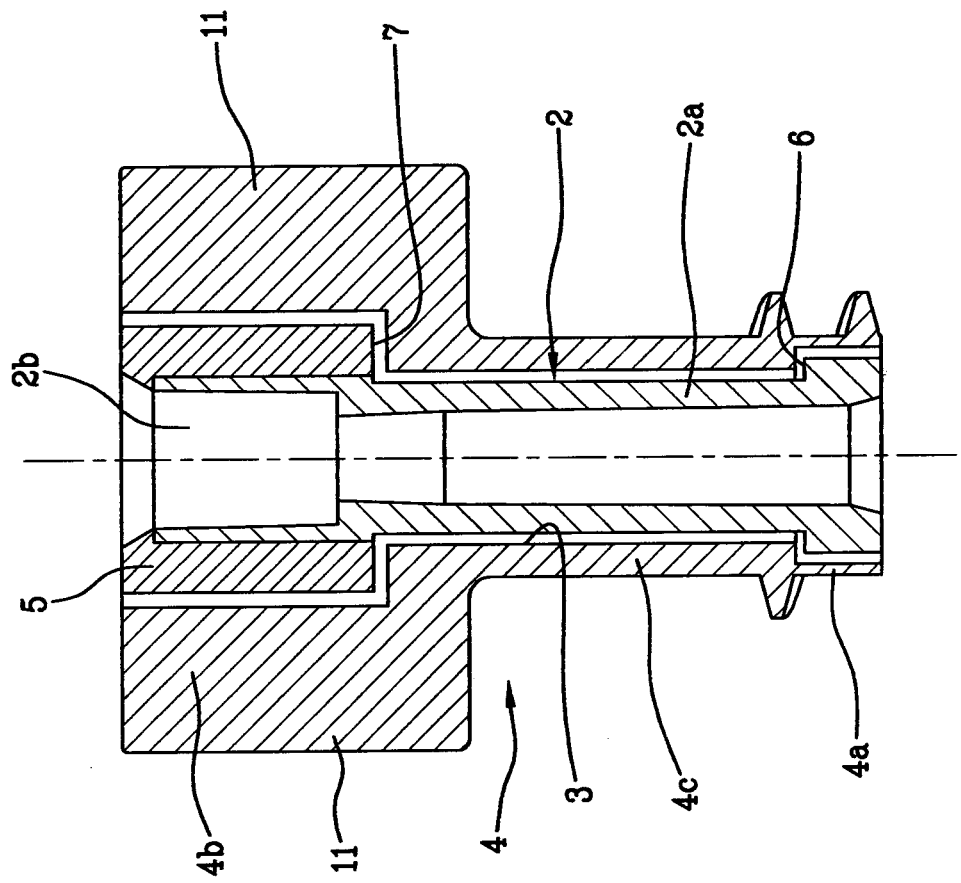

FIG. 25 is a section along plane XXV-XXV of FIG. 24.

FIG. 26 shows a longitudinal section of a fifth embodiment of the medical connector of the invention.

FIG. 27 is a section along plane XXVII-XXVII of FIG. 26.

FIG. 28 is a longitudinal section of a sixth embodiment of the medical connector of the invention.

FIG. 29 is a section along line XXIX-XXIX of FIG. 28.

DETAILED DESCRIPTION

With reference to figures from 1 to 5, 1 denotes in its entirety a medical connector which can be used for coupling a fluid transport tube (not illustrated), such as for example a tube for transporting extracorporeal blood, with a port for passage of fluid (not illustrated) such as for example a port of a device for extracorporeal blood treatment (blood port, either inlet or outlet, of a dialyser). In particular the fluid transport tube can be a flexible tube, of a type used in a dialysis set of known type. In the specific case illustrated herein, the medical connector comprises a female luer connector and the port for the fluid passage (not illustrated) comprises a male luer attachment.

In the specific embodiment, the medical connector can serve for connecting an end of a blood line (arterial or venous) with a blood port (inlet or outlet) of a membrane blood treatment unit of known type (dialyser, hemofilter, hemodiafilter, therapeutic plasma exchanger, artificial liver, etc.).

The medical connector 1 comprises a first tubular body 2, or internal tubular body, having at least a first end portion 2a, a second end portion 2b opposite the first end portion 2a, and an intermediate portion 2c arranged between the first and the second end portion 2a and 2b. The first tubular body 2 can define, as in the specific embodiment, a longitudinal axis. Optionally the first tubular body 2 can have an axial-symmetric form about a longitudinal axis. Optionally the first tubular body can be, as in the specific case, a solid of revolution.

The first end portion 2a defines at least a part of an internal sealing surface having a truncoconical shape with a predetermined degree of conicity (luer conicity). The internal surface is configured, in a known way, for fluid sealing coupling with a corresponding external counter-surface, for example truncoconical, borne by an external element (of known type and not illustrated), such as for example an access port to a blood chamber of a dialyser (or other blood treatment device of the semipermeable membrane type) provided with a male luer connector.

The second end portion 2b defines at least a part of a connecting zone configured for connection with a fluid transport tube. The connecting zone comprises a seating for receiving an end portion of a tube (for example a flexible tube of an extracorporeal blood line, arterial or venous). In an assembly stage of the apparatus which uses the medical connector, for example assembly of the extracorporeal blood line, the end portion is inserted in the seating and stably connected to the connector in a known way, by means of any one of the known techniques for connecting ends of tubular bodies (for example by welding or gluing). The seating can define, as in the specific case, a flared truncoconical entry part for the tube, a true and proper connecting part having a cylindrical or slightly truncoconical shape, and a terminal part bearing an abutment which functions as a stop for insertion of the tube.

The connector 1 (in particular the tubular body 2) comprises a radial projection 3 borne by the intermediate portion 2c. The radial projection 3 has a maximum external diameter which can be comprised, for example, between 8 and 18 millimeters. In the specific case the external diameter is about 13 millimeters. The radial projection 3 is, optionally, annular (complete). The radial projection 3 can be delimited axially, as in the present embodiment, by two opposite surfaces, each having a circular crown shape which is perpendicular to a longitudinal axis of the first tubular body 2.

The connector 1 comprises a second tubular body 4, or external tubular body, having a third end portion 4a and a fourth end portion 4b, opposite one another. The third portion of end 4a at least partially surrounds the first end portion 2a. The fourth end portion 4b at least partially surrounds the second end portion 2b and the intermediate portion 2c.

The third end portion 4a has, in the illustrated example, a threaded external coupling surface. The threaded coupling surface is configured, in a known way, for coupling with a corresponding threaded internal surface borne on the external element (for example the male luer connector) which couples to the connector 1 and which also bears the external opposite surface (for example truncoconical with a luer connector) which is fluid-sealed.

The second tubular body 4 is free to rotate with respect to the first tubular body 2 about a rotation axis which is coaxial to the external screw-coupling surface. The rotation axis can further coincide with the longitudinal axis of the first tubular body 2 and/or with the longitudinal axis of the second tubular body 4. The fourth end portion 4b has a minimum internal diameter which is greater (for example by about a millimeter) than the maximum external diameter of the radial projection 3. This allows, during the assembly stage of the connector 1, easy insertion of the first tubular body 2 (bearing the projection 3) internally of the second tubular body 4 and, during the use stage, allows free reciprocal rotation of a tubular body with respect to another. In particular the above-described insertion during the assembly stage can be performed without any interference, jointing or forcing or other type of resistance to the insertion.

The connector 1 comprises an insert 5 solidly connected to the fourth end portion 4b of the second tubular body. The insert 5 can be an element made separately from the second tubular body 4 and thus coupled to the second tubular body 4 in a subsequent assembly stage. The insert 5 can further be an element made from a pre-element blank which is made together with and in a single piece with the second tubular body 4 first (for example during a same injection-moulding stage of plastic material) and which then, after insertion of the first tubular body 2 bearing the projection internally of the second tubular body 4, is modified (for example by plastic deformation) up until it forms the definitive insert 5 (as in the example of figures from 20 to 23).

Figure 1:
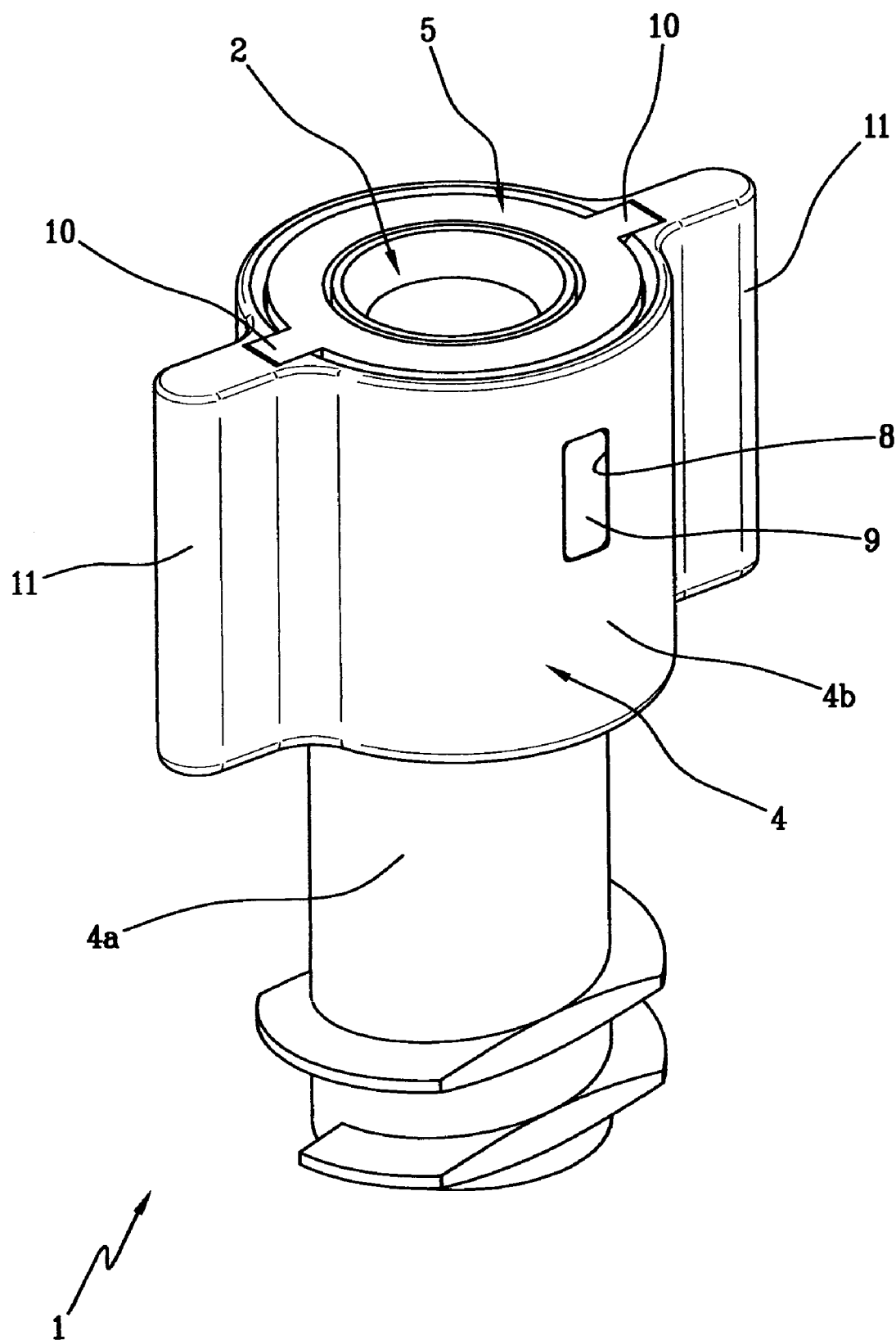
FIG. 1 is a perspective view of a medical connector made according to the present invention.
Figure 3:
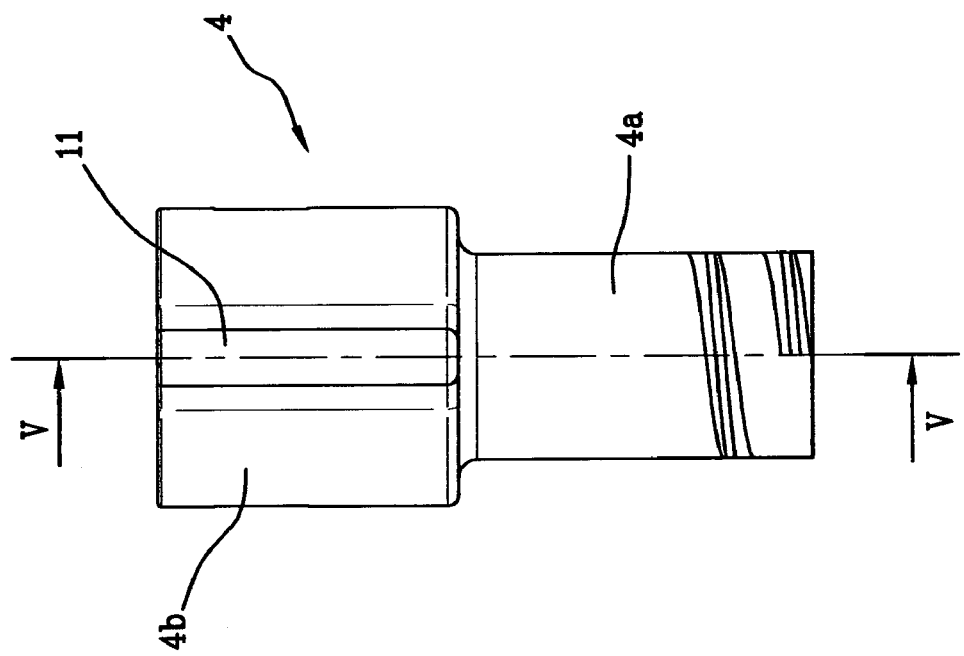
FIG. 3 is a lateral view of the connector of FIG. 1.
Figure 2:
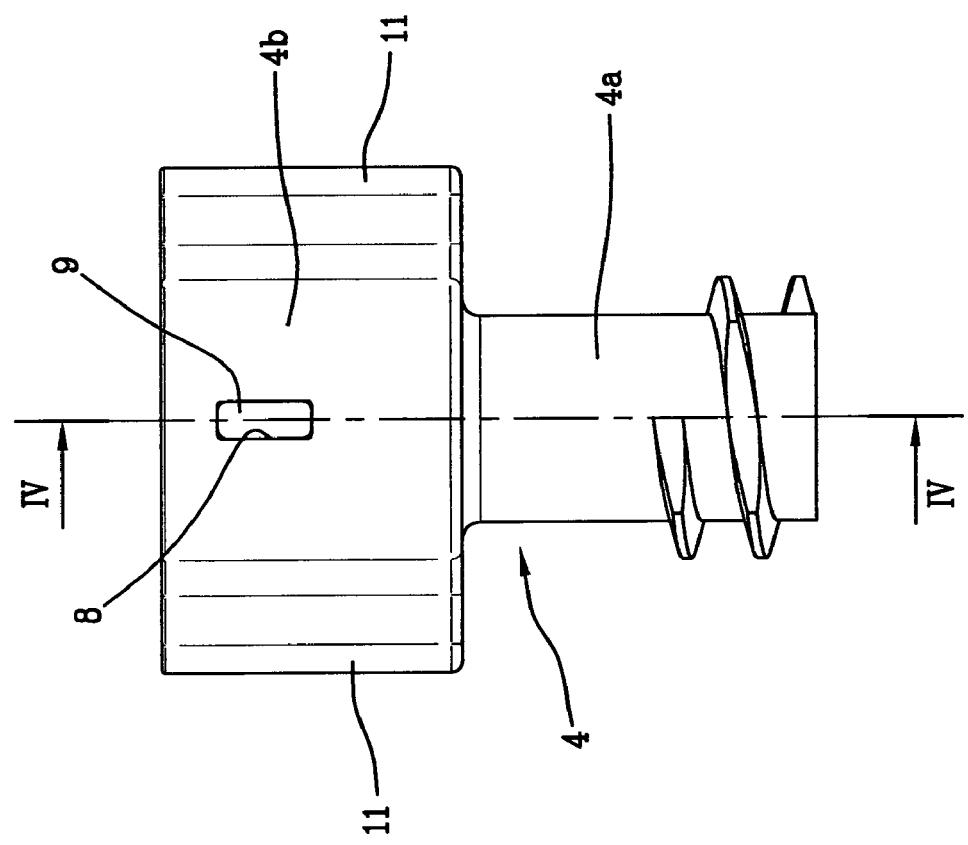
FIG. 2 is a frontal view of the connector of FIG. 1.
Figure 5:
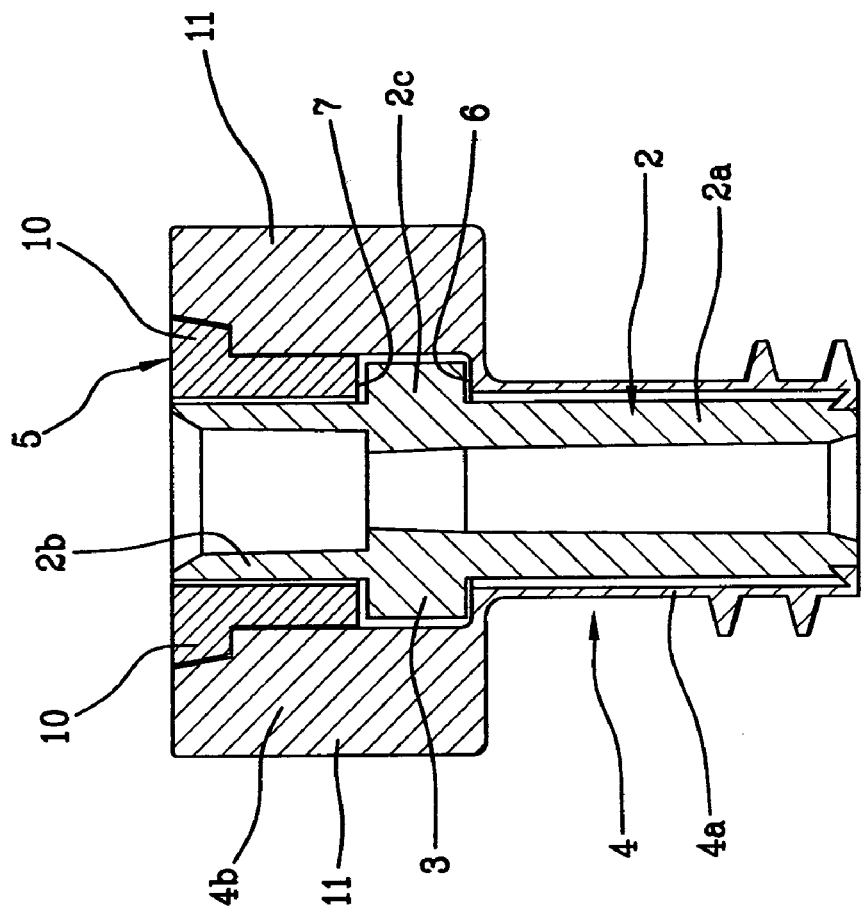
FIG. 5 is a section along line V-V of FIG. 3.
Figure 4:
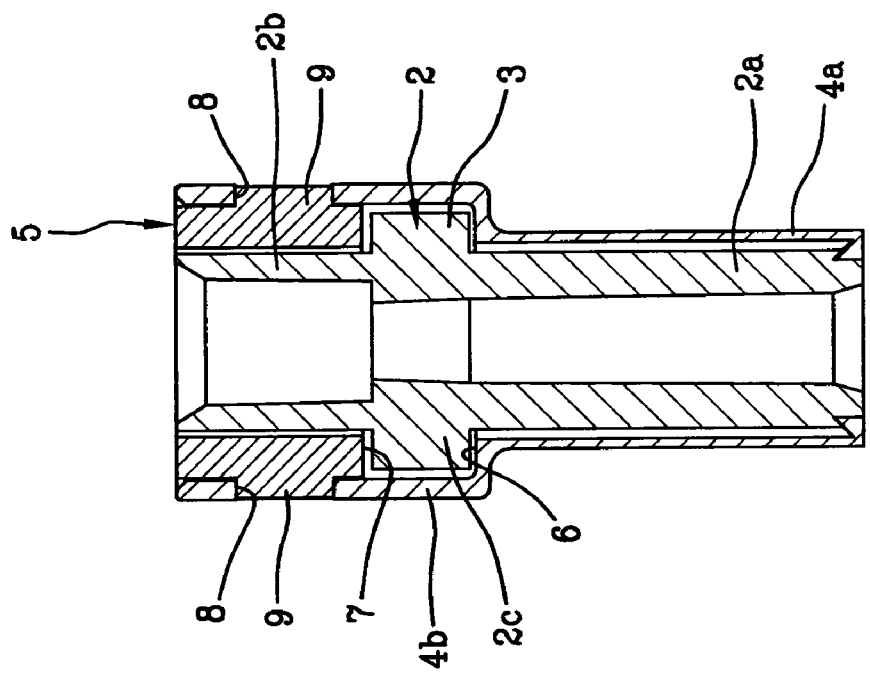
FIG. 4 is a section along line IV-IV of FIG. 2.
Figure 13:
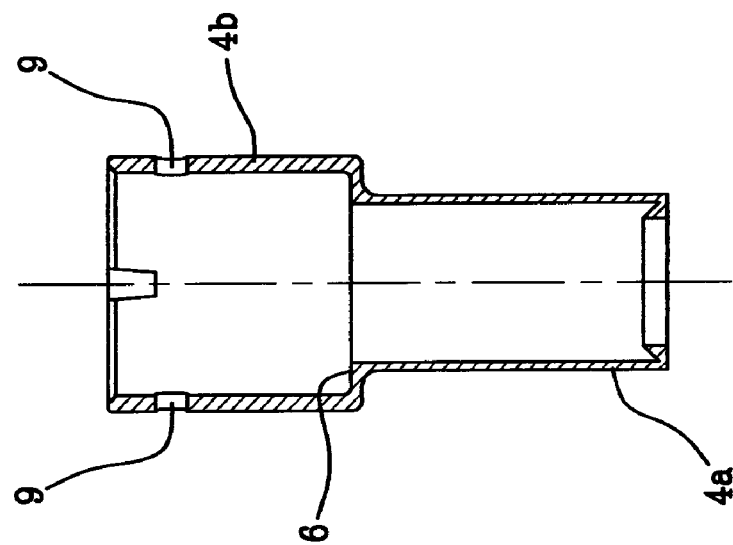
Figure 12:
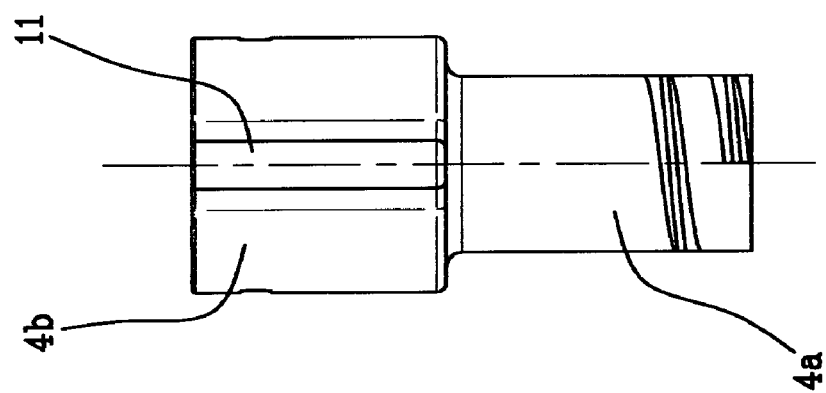
Figure 11:
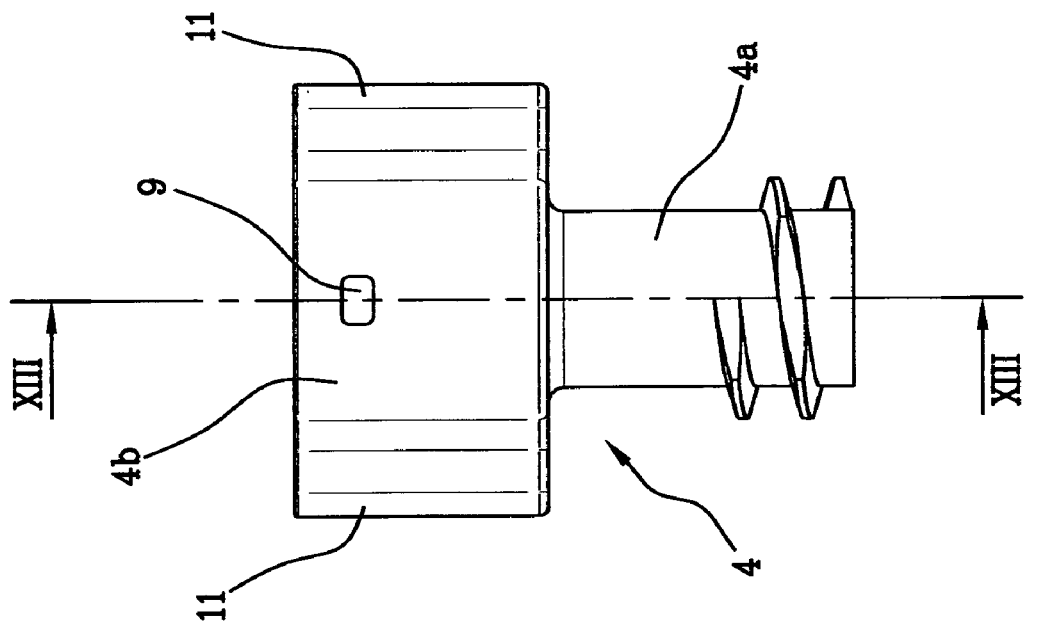
Figure 17:
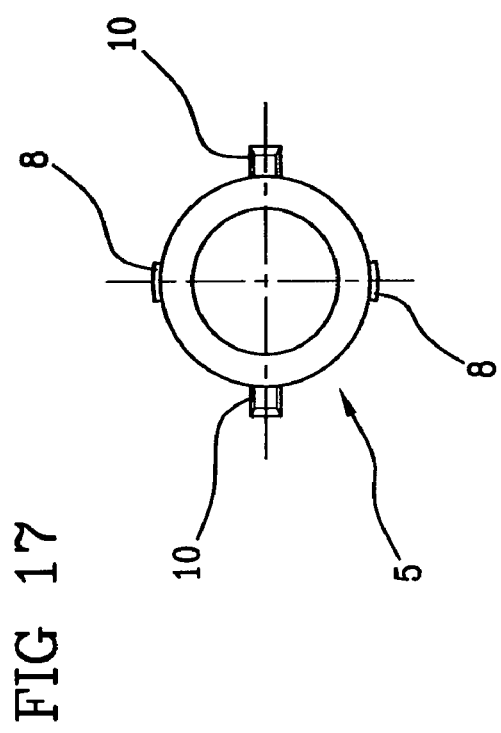
Figure 18:
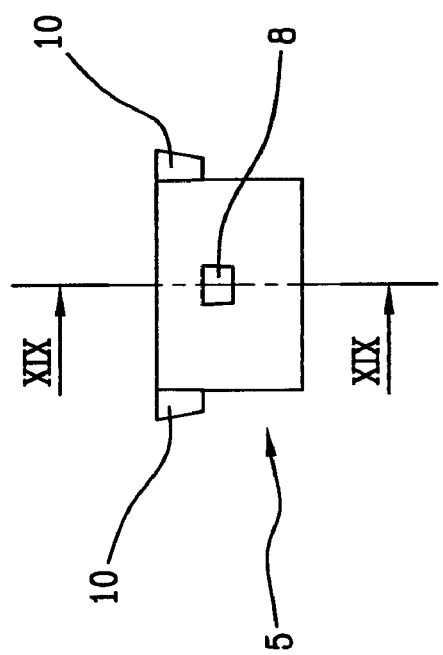
Figure 19:
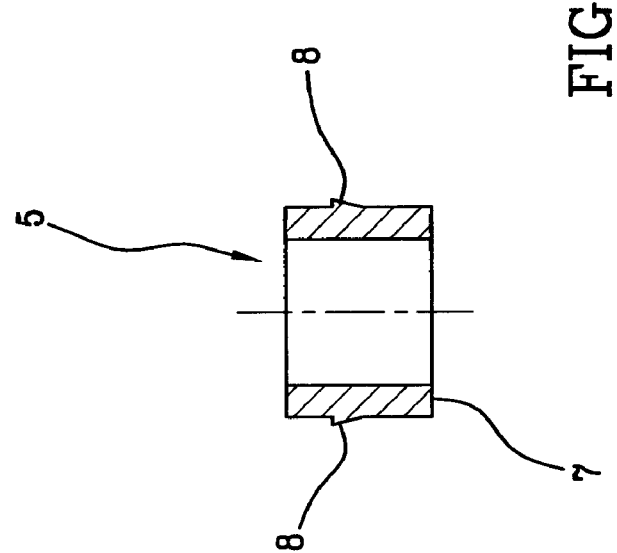

The connector 1 comprises a first stop surface 6 borne by the second tubular body 4. The first stop surface 6 is configured for interacting with the radial projection 3 such as to limit an axial displacement of the first tubular body 2 with respect to the second tubular body 4 in a first axial displacement direction which goes from the fourth end position 4b to the third end position 4a (with reference to FIGS. 4 and 5, this first displacement direction is in a downwards direction).

The first stop surface 6 can comprise, as in the specific case, a front surface, substantially perpendicular to the longitudinal axis of the second tubular body 4. The stop surface 6 can be, in particular, in the shape of a circular crown. The surface 6 can be, optionally, directly facing, in an axial direction parallel to the longitudinal axis of the first tubular body 2 and/or the second tubular body 4, the radial projection 3, in particular a first axial end of the radial projection 3. In an uncoupling stage of the connector 1 (female luer) from the external counter-connector (male luer), the first stop surface 6 can interact contactingly with the radial projection 3 such that the second tubular body 4 (external) can axially displace the first tubular body 2 (internal) and thus detach the internal truncoconical sealing surface of the connector 1 from the corresponding external truncoconical sealing surface of the counter-connector.

The connector 1 comprises a second stop surface 7 which, in the specific case, is borne by the insert 5. The second stop surface 7 is configured to interact with the radial projection 3 such as to stop or limit an axial displacement of the first tubular body 2 with respect to the second tubular body 4 in a second axial displacement opposite the first direction.

The second stop surface 7 can comprise, as in the specific case, a front surface, substantially perpendicular to the longitudinal axis of the first tubular body 2 and/or the second tubular body 4. Optionally the second stop surface 7 can be in the form of a circular crown. The second stop surface 7 can optionally be directly facing the radial projection 3, in an axial direction which is parallel to the longitudinal axis of the first tubular body 2 and/or the second tubular body 4, in particular facing a second axial end of the radial projection 3 which can be, as in the specific case, opposite the first axial end.

During the coupling stage of the connector 1 (female luer) to the external counter-connector (male luer), the second stop surface 7 can interact contactingly with the radial projection 3 such that the second tubular body (external) can axially displace the first tubular body 2 (internal) and thus bring the internal truncoconical sealing surface of the connector 1 to sealing close the corresponding external truncoconical external surface of the counter-connector.

The fourth end portion 4b of the second tubular body optionally comprises at least a wall provided with at least a recess 8. In the specific case the fourth end portion 4b exhibits at least two recesses 8 which can be arranged, as in the specific case, diametrically one opposite the other.

The insert 5 is provided with a least a protuberance, or pawl, or a blocking organ or a retaining tooth 9 inserted in the recess 8. The pawl 9 is optionally joint-coupling in the recess 8. In particular the pawl 9 is snap-fit coupled in the recess 8. In the specific case the insert 5 exhibits at least two pawls 9 which can be arranged, for example, diametrically opposite one another. More than two pawls 9 can be predisposed. The pawls 9 can also be arranged staggered to one another or on different diameters or on different perpendicular planes with respect to the longitudinal axis of the external tubular body 4, etc.

Each pawl 9 is coupled to a corresponding recess 8. Each recess 8 can comprise, in the example, a window afforded on the wall. The window is a through-window, i.e. it crosses the whole thickness of the wall. In particular each pawl 9 projects radially from an external surface of the insert 5 for insertion in the recess 8. The recesses 8 are optionally distanced from one another in a circumferential direction.

The insert 5 has at least a reference element 10 and the second tubular body 4 has at least a reference counter-element. The reference element 10 is coupled to the reference counter element by angular positioning of the insert 5 with respect to the second tubular body 4 in a coupling position in which each recess 8 and the corresponding pawl 9 are coupled to one another.

The reference element 10 and the counter-reference element comprise, in this particular embodiment, a pair of elements formed by a radial projection (emerging from the insert 5) and by a seating (afforded in the second tubular body 4, in particular on an internal surface of the body) configured to receive the projection. As mentioned, the coupling of the reference means and the corresponding counter-reference means facilitates the correct angular positioning of the insert 5 with respect to the second external tubular body 4, so that the means for axially blocking (represented in the embodiment by the joint between the pawl 9 and the recess 8) are correctly activated. Each seating has a frontal opening for insertion of the projection in an axial direction. In the specific embodiment the reference means and the counter-reference means also have the task of operating in favour of the rotational solidarity between the insert 5 and the external tubular body 4, ensuring or in any case collaborating to prevent or limit the rotation.

Note that the means for axially blocking can firstly at least partly collaborate, as in the illustrated example, to facilitate rotational solidarity of the insert 5 and the external body 4, and secondly (as in the illustrated example) it is possible that neither the means for axially blocking nor the means for angular positioning can exert any substantial influence, at least directly, on the relationship between the internal tubular body 2 and the insert 5 or the external tubular body 4 with regards to rotation. In other words, the means for axially blocking and the means for angular positioning do not influence the rotation coupling between the internal tubular body 2 and the insert 5 or the external tubular body 4, thus leaving the internal tubular body 2 completely free to rotate (about the longitudinal axis thereof) with respect to insert 5 or the external tubular body 4. The insert 5 can even, as in the specific case, have an internal surface that surrounds the second end portion 2b of the first tubular body 2 and which is facing at a certain distance therefrom. The above-cited means for axially blocking and/or angular positioning can be configured such as to axially block the insert 5 with respect to the second external tubular body 4 either absolutely, or in such a way as to leave a predetermined axial play of the order, for example of about a millimeter.

The fourth end position 4b can comprise a manual gripping zone which, as in the specific case, can be provided with a plurality of tabs 11 which project radially towards the outside and are distanced from one another in a circumferential direction. Optionally, on each zone of the fourth end zone comprised, in a circumferential direction, between two adjacent tabs 11, at least a recess 8 (window) is afforded. Also, as in the illustrated example, each seating predisposed to receive the corresponding radial projection 10 of angular positioning is located, radially, at a tab 11.

Figures from 6 to 19 illustrate a second embodiment in which the elements which are alike to the first embodiment have been denoted using the same numbers. Figures from 8 to 19 separately show the various elements which make up the assembly of FIGS. 6 and 7. This second embodiment differs from the first embodiment essentially in that each pawl 9 has a slightly different shape. In this case each pawl has an inclined front surface which facilitates axial insertion of the pawl 9 in the recess 8 during assembly. In this case too the pawl 9 has the function of preventing or limiting backward axial motion, inverse to the insertion direction, of the insert 5 with respect to the external tubular body 4, possibly leaving a predetermined amount of axial play.

With reference to figures from 20 to 23 (in which the elements which are also in the preceding figures are denoted using the same numbers), the connector is provided with an insert 5 which instead of being coupled by snap-fit, is obtained by plastic deformation (hot or cold) of a pre-element in a single piece with the second tubular body 4. The pre-element is illustrated in FIGS. 22 and 23 and denoted by 12. The pre-element 12 is made in a single piece with the external tubular body 4, for example during the stage of injection moulding of plastic material.

The pre-element 12 can comprise, as in the specific case, an annular body which surrounds a central opening of the body 4; the central opening is the opening for free introduction (without axial resistances), during the assembly stage, of the first internal tubular body 2. In this case, then, the insert 5 comprises a portion of plastically-deformed material, in which the deformed material is the material of the second tubular body 4.

Other embodiments can be provided in which the insert 5 is glued or welded to the fourth end portion 4b. In further embodiments, the insert 5 can be screw-coupled to the fourth end portion 4b, or can be coupled thereto by a friction coupling.

In use, the medical connector is coupled to the corresponding counter-connector by a screw-coupling. This coupling is set up by means of a rotation of the connector element bearing the threaded screwing surface, i.e. the external tubular body 4 (and the insert 5 which is solidly in rotation therewith), without rotation of the internal tubular body 2 which bears the fluid-sealed surface. The rotation includes, as is known, an axial displacement of the external tubular body 4, which is followed by an axial displacement of the internal tubular body 2, which is axially drawn by virtue of the presence of the radial projection 3 to enable fluid-sealed coupling of the converging sealing surfaces (with a predetermined degree of luer conicity).

For disconnection an inversely-direction rotation will be made, with consequent axial displacement of both the external tubular body 4 and the internal tubular body 2.

FIGS. 24 and 25 illustrate a medical connector (keeping the same numbering for the same elements in the connectors previously described) in which the insert 5 is coupled to the internal tubular body 2 instead of to the external tubular body 4. In this case the radial projection 3 is associated to an internal surface of an intermediate portion 4c of the external tubular body 4 and projects radially internally. The end portion 2a of the first internal tubular body 2 has an end flange which bears the stop surface 6.

The radial projection 3 has a minimum internal diameter which is greater than a maximum external diameter of the second end portion 2b. The first stop surface 6 is configured to interact with the radial projection 3 such as to limit an axial displacement of the second tubular body 4 with respect to the first tubular body 2 in a first axial displacement direction which goes from the second end portion 2b to the first end portion 2a. The second stop surface 7 is borne by the insert 5 and is configured to interact with the radial projection 3 such as to limit an axial displacement of the second tubular body 4 with respect to the first tubular body 2 in a second axial displacement direction which is opposite the first axial displacement direction. The insert 5 has an external surface which is surrounded by the fourth end portion 4b of the second tubular body 4 and faces the fourth end portion 4b at a certain distance therefrom. The insert 5 is solidly connected to the second end portion 2b of the first tubular body 2 in a similar manner as previously disclosed for the insert being solidly connected to the fourth end portion 4b of the second tubular body 4. The insert 5 comprises a portion of a plastically-deformed material where the material is the same as a material of which the first tubular body 2 is made.

FIGS. 26 and 27 illustrate a medical connector (keeping the same numbering for the same elements in the connectors previously described) in which means for reducing dragging friction are included between the second stop surface 7 and the radial projection 3. In particular the means for reducing the friction are configured to reduce the friction during a relative displacement of the insert and the projection 3 in a circumferential direction, such as for example during an unscrewing or screwing of the connector 1 to a corresponding counter-connector. The means for reducing the friction can comprise, as in the specific case, at least a spacer element 13 interposed between the second stop surface 7 and the radial projection 3. This spacer element 13 can optionally comprise at least a protuberance emerging from the second stop surface 7 (as in the example of FIGS. 26 and 27) or a front surface (facing in an axial direction to the second stop surface 7) of the radial projection 3 (as in the following example of FIGS. 28 and 29).

FIGS. 28 and 29 illustrate a further embodiment of the medical connector of the invention (keeping the same numbering for the same elements in the connectors previously described) in which the means for reducing the draggning friction comprise, also in this case, a spacer element 13 which is however, in this specific case, solidly connected (or integrated, or made in a single piece by moulding of plastic material) to the radial projection 3, while in the preceding case it was solidly connected (or integrated, or made in a single piece by moulding of plastic material) to the second stop surface 7. A spacer element can be realised having a first part which is solidly connected to the stop surface 7 and a second part which is solidly connected to the radial projection 3, in which the first and the second part can collaborate to reduce the friction, both in a reciprocal contact relationship (operating along the same circumferential operating zone), and not in contact with one another (operating along two distinct circumferential operating zones).

The spacer element 13 can have an annular shape (as in the illustrated examples); or it can comprise a series of elements which are angularly distinct and arranged, for example, in a ring-fashion; or it can comprise a layer of an anti-friction material predisposed between the second stop surface 7 and the radial projection 3; or it can comprise one or more solid or fluid elements interposed, but not solidly constrained either to the insert 5 or the radial projection 3); or it can comprise one or more rolling bodies configured to give rise to a revolving friction between the second stop surface 7 and the radial projection 3. The spacer element further comprises, in an example which is not illustrated, a crowning realised on the second stop surface 7 and/or a front surface (axially facing the second stop surface) of the radial projection 3. The spacer element 13 can have, as in the illustrated examples, a median section (made according to a section plane passing through the longitudinal axis of the connector 1) having a roughly rectangular shape, or (in order further to reduce the friction) a rounded shape (for example semi-circular or semi-elliptic, or having a circular sector, or other rounded shapes), or a triangular or a trapezoid shape, etc.

The examples of figures from 26 to 29 relate to the predisposition of anti-friction means to a connector which is similar to the one of FIGS. 16 to 19. However all the anti-friction means described above might be similarly applied to all the embodiments described herein.

The insert 5 can be, as in the specific case, coupled to the end portion 2b of the tubular body 2 by forcing, by a friction coupling insertion, or with any other coupling system described herein above with reference to the portion of end 4b of the external body 4. In this case too, as in the preceding cases, the insertion of the first internal tubular body 2 in the second external tubular body 4 during the connector assembly stage is done with no interference, obstacles or other axial resistance (if not the contact between the projection 3 and the stop surface 6 which determines the end run of the insertion stage).

The insert 5 is optionally made of a material (for example PBT or POM) which is stiffer than the material (for example PP) which the second tubular body 4 is made of. Further, the insert is optionally made of a stiffer material than that (for example PVC) of which the first tubular body 2 is made.

The invention claimed is:
1. A medical connector, comprising:
a first tubular body having at least a first end portion, a second end portion located opposite the first end portion and an intermediate portion arranged between the first end portion and the second end portion, the first end portion defining at least a part of a truncoconical internal seal surface having a predetermined degree of conicity, the second end portion defining at least a part of a connection zone configured for connection with a fluid transport tube;

a radial projection borne by the intermediate portion, the radial projection having a maximum external diameter;

a second tubular body having a third end portion and a fourth end portion which are opposite one another, the third end portion at least partly surrounding the first end portion, the fourth end portion at least partly surrounding the second end portion and the intermediate portion, the third end portion having an external screw-coupling surface, the second tubular body being free to rotate with respect to the first tubular body about a rotation axis which is coaxial to the external screw-coupling surface; the fourth end portion having a minimum internal diameter which is greater than the maximum external diameter of the radial projection;

an insert which is solidly connected to the fourth end portion of the second tubular body;

a first stop surface borne by the second tubular body, the first stop surface being configured to interact with the radial projection such as to limit an axial displacement of the first tubular body with respect to the second tubular body in a first axial displacement direction which goes from the fourth end portion to the third end portion;

a second stop surface borne by the insert, the second stop surface being configured to interact with the radial projection such as to limit an axial displacement of the first tubular body with respect to the second tubular body in a second axial displacement direction which is opposite the first axial direction.

2. The connector of claim 1, wherein the fourth end portion of the second tubular body comprises at least a wall provided with at least a recess, the insert being provided with at least a pawl joint-coupled in the recess.

3. The connector of claim 2, wherein the recess comprises a window afforded on the wall.

4. The connector of claim 2, wherein the pawl is snap-fitted in the recess.

5. The connector of claim 2, wherein the pawl projects radially from an external surface of the insert for inserting in the recess.

6. The connector of claim 2, wherein the wall is provided with a plurality of recesses which are distanced from one another in a circumferential direction, the insert being provided with a plurality of pawls, each coupled to a corresponding recess.

7. The connector of claim 6, wherein each recess comprises a window afforded on the wall and wherein the fourth end portion comprises a manual gripping zone provided with a plurality of tabs projecting radially externalwise and distanced from one another in a circumferential direction, at least a window of the windows being afforded in each zone comprised between two adjacent tabs.

8. The connector of claim 2, wherein the insert has at least a reference element and the second tubular body has at least a reference counter-element, the reference element being coupled to the reference counter-element by angular positioning of the insert with respect to the second tubular body in a coupling position in which the recess and the pawl are coupled to one another.

9. The connector of claim 8, wherein the reference element and the counter-reference element comprise a pair of elements formed by a projection projecting radially and by a seating configured to receive the projection, the seating having a frontal opening for insertion of the projection in an axial direction.

10. The connector of claim 1, wherein the insert has an internal surface which surrounds the second end portion of the first tubular body and which faces the second end portion at a certain distance therefrom.

11. The connector of claim 1, wherein the insert is glued or welded to the fourth end portion.

12. The connector of claim 1, wherein the insert is screw-coupled to the fourth end portion.

13. The connector of claim 1, wherein the insert is friction-coupled to the fourth end portion.

14. The connector of claim 1, wherein the insert comprises a portion of plastically-deformed material, the material being a same material as the second tubular body.

15. The connector of claim 1, wherein the insert is made of a more rigid material than a material of which the second tubular body is made.

16. The connector of claim 1, wherein the insert is made of a stiffer material than a material of which the first tubular body is made.

17. An extracorporeal blood circuit, comprising at least a blood transport line having at least an end having a medical connector made according to claim 1.

18. A medical connector, comprising:
a first tubular body having a first end portion and a second end portion which are opposite one another, the first end portion defining at least a part of a truncoconical internal seal surface having a predetermined conicity, the second end portion defining at least a part of a connecting zone configured for connecting to a fluid transport tube, the second end portion having a maximum external diameter;

a second tubular body having a third end portion, a fourth end portion opposite the third end portion, and an intermediate portion arranged between the third end portion and the fourth end portion, the third end portion at least partly surrounding the first end portion, the fourth end portion at least partly surrounding the second end portion, the third end portion having an external screw-coupling surface, the second tubular body being free to rotate with respect to the first tubular body about a rotation axis which is coaxial to the external screw-coupling surface;

a radial projection borne by the intermediate portion, the radial projection having a minimum internal diameter which is greater than a maximum external diameter of the second end portion;

an insert which is solidly connected to the second end portion of the first tubular body;

a first stop surface borne by the first tubular body, the first stop surface being configured to interact with the radial projection such as to limit an axial displacement of the second tubular body with respect to the first tubular body in a first axial displacement direction which goes from the second end portion to the first end portion;

a second stop surface borne by the insert, the second stop surface being configured to interact with the radial projection such as to limit an axial displacement of the second tubular body with respect to the first tubular body in a second axial displacement which is opposite the first axial displacement direction.

19. The connector of claim 18, wherein the insert has an external surface which is surrounded by the fourth end portion of the second tubular body and faces the fourth end portion at a certain distance therefrom.

20. The connector of claim 18, wherein the insert is glued or welded to the second end portion.

21. The connector of claim 18, wherein the insert is screw-coupled to the second end portion.

22. The connector of claim 18, wherein the insert is friction-coupled to the second end portion.

23. The connector of claim 18, wherein the insert comprises a portion of a plastically-deformed material, the material being the same as a material of which the first tubular body is made.

24. The connector of claim 18, wherein the insert is made of a stiffer material than a material of which the first tubular body is made.

25. The connector of claim 18, wherein the insert is made of a stiffer material than a material of which the second tubular body is made.

26. The connector of claim 18, comprising means for reducing a dragging friction between the second stop surface and the radial projection.

27. The connector of claim 26, wherein the means for reducing the friction comprise at least a spacer element interposed between the second stop surface and the radial projection.

28. The connector of claim 27, wherein the spacer element comprises at least a protuberance emerging from the second stop surface or from a frontal surface of the radial projection.

29. The connector of claim 27, wherein the at least a spacer element has an annular shape.

30. An assembly method of a medical connector, the method comprising stages of:
- providing a first tubular body having at least a first end portion, a second end portion located opposite the first end portion, an intermediate portion arranged between the first end portion and the second end portion, the first end portion defining at least a part of a truncoconical internal seal surface having a predetermined degree of conicity, the second end portion defining at least a part of a connection zone configured for connecting to a fluid transport tube; the intermediate portion bearing a radial projection having a maximum external diameter;
- providing a second tubular body, the second tubular body having a third end portion and a fourth end portion which are opposite one another, the third end portion having an external screw-coupling surface, the fourth end portion having a minimum internal diameter which is greater than a maximum external diameter of the radial projection;
- axially inserting the first tubular body internally of the second tubular body without axial interference, so that the third end portion at least partly surrounds the first end portion, the fourth end portion at least partly surrounds the second end portion and the intermediate portion, the second tubular body is free to rotate with respect to the first tubular body about a rotation axis which is coaxial to the external screw-coupling surface, and a first stop surface borne by the second tubular body is configured to interact with the radial projection in such a way as to limit an axial displacement of the first tubular body with respect to the second tubular body in a first axial displacement direction which goes from the fourth end portion to the third end portion;
- solidly connecting an insert to the fourth end portion of the second tubular body, so that a second stop surface borne by the insert is configured to interact with the radial projection in such a way as to limit an axial displacement of the first tubular body with respect to the second tubular body in a second axial displacement direction which is opposite the first axial displacement direction.

31. A method for assembling a medical connector, the method comprising stages of:
- providing a first tubular body having at least a first end portion, a second end portion located opposite the first end portion, the first end portion defining at least a part of a truncoconical internal seal surface having a predetermined degree of conicity, the second end portion defining at least a part of a connection zone configured for connection with a fluid transport tube, the second end portion having a maximum external diameter;
- providing a second tubular body, the second tubular body having a third end portion, a fourth end portion opposite the third end portion, and an intermediate portion arranged between the third end portion and the fourth end portion, the third end portion having an external screw-coupling surface, the intermediate portion bearing a radial projection having a minimum internal diameter which is greater than a maximum external diameter of the second end portion;
- axially inserting the first tubular body internally of the second tubular body without axial interference, so that the third end portion at least partly surrounds the first end portion, the fourth end portion at least partly surrounds the second end portion, the second tubular body is free to rotate with respect to the first tubular body about a rotation axis which is coaxial to the external screw-coupling surface, and a first stop surface borne by the first tubular body is configured to interact with the radial projection in such a way as to limit an axial displacement of the second tubular body with respect to the first tubular body in a first axial displacement direction which goes from the second end portion to the first end portion;
- solidly connecting an insert to the second end portion of the first tubular body, so that a second stop surface borne by the insert is configured to interact with the radial projection such as to limit an axial displacement of the second tubular body with respect to the first tubular body in a second axial displacement direction opposite the first axial displacement direction.

\* \* \* \* \*